United States Patent
Sugimoto et al.

[19]

[11] Patent Number: 6,062,065
[45] Date of Patent: May 16, 2000

[54] METHOD AND APPARATUS IN GAS CHROMATOGRAPHY FOR INTRODUCING A SAMPLE

[75] Inventors: Kiyoshi Sugimoto, Osaka; Haruhiko Miyagawa, Tokyo; Katsuhiro Nakagawa, Kyoto, all of Japan

[73] Assignees: Shimadzu Corporation, Kyoto; Osaka Pharmaceutical Association, Osaka, both of Japan

[21] Appl. No.: 09/080,818

[22] Filed: May 18, 1998

[30] Foreign Application Priority Data

Jun. 23, 1997 [JP] Japan .................................... 9-182976

[51] Int. Cl.[7] .................................................... G01N 30/04
[52] U.S. Cl. ........................ 73/23.42; 73/23.35; 96/101; 96/105
[58] Field of Search ................................ 73/23.35, 23.42; 96/101, 105

[56] References Cited

U.S. PATENT DOCUMENTS 5,339,673  8/1994  Nakagawa et al. ................. 73/23.42 X
5,672,810  9/1997  Shibamoto et al. ................. 73/23.42 X
5,779,765  7/1998  Grob et al. ........................ 73/23.41 X

OTHER PUBLICATIONS

Principles and Practice of Gas Chromatography, Robert L. Pecsok, ed. John Wiley and Sons, Inc., 1959, pp. 40–47.

*Primary Examiner*—Daniel S. Larkin
*Attorney, Agent, or Firm*—Majestic, Parsons, Siebert & Hsue P.C.

[57] ABSTRACT

A tubular insert with a small internal volume is disposed inside the vaporization chamber at the inlet of a capillary column of a gas chromatograph such that the sample with a solvent injected into the vaporization chamber is carried by a carrier gas through the insert into the column. The internal volume of the insert is such that the retention time of the carrier gas through the insert is less than 4 seconds. A heater is controlled to maintain the temperature inside the vaporization chamber within a specified range above the boiling point of the solvent as the sample is injected into the vaporization chamber, and this temperature is subsequently raised to a final temperature above the boiling points of the components to be analyzed. The carrier gas pressure is temporarily increased for better efficiency as the sample is injected.

18 Claims, 8 Drawing Sheets

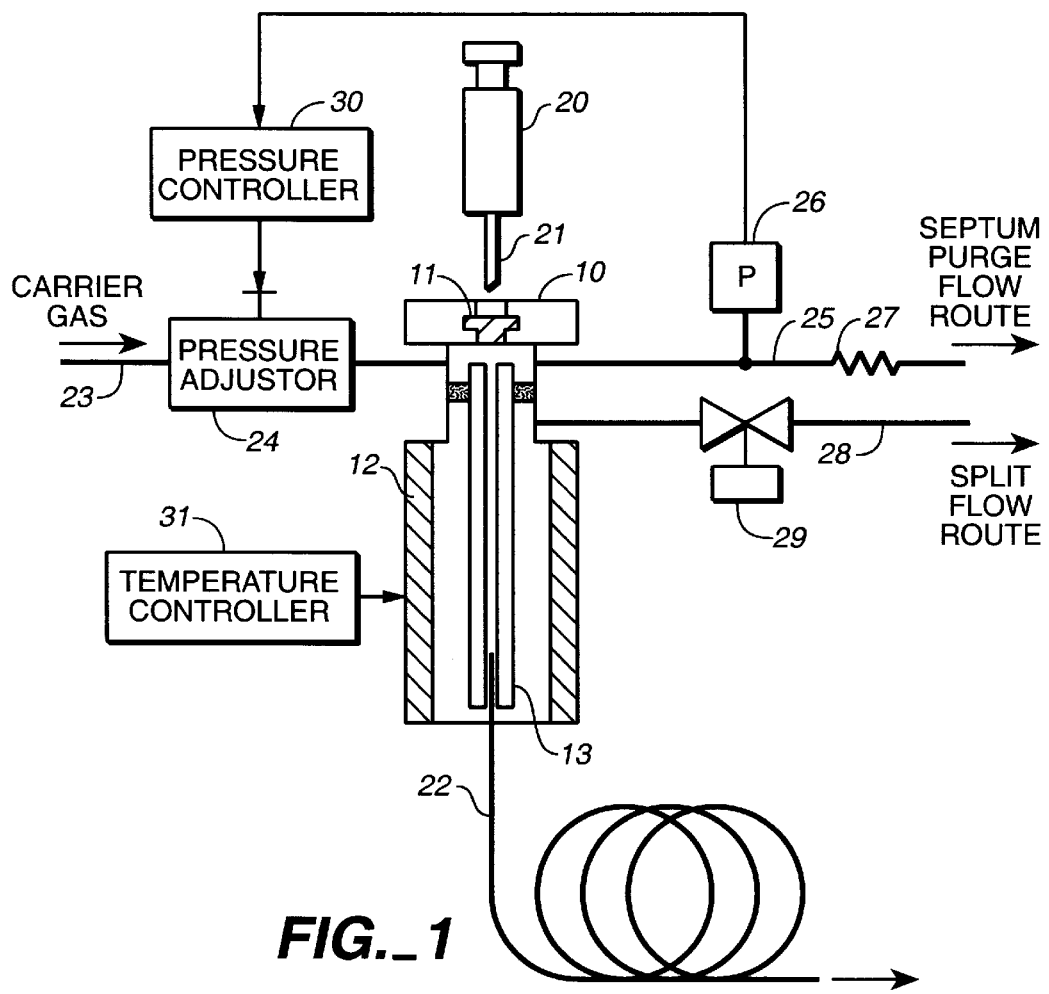
FIG._1
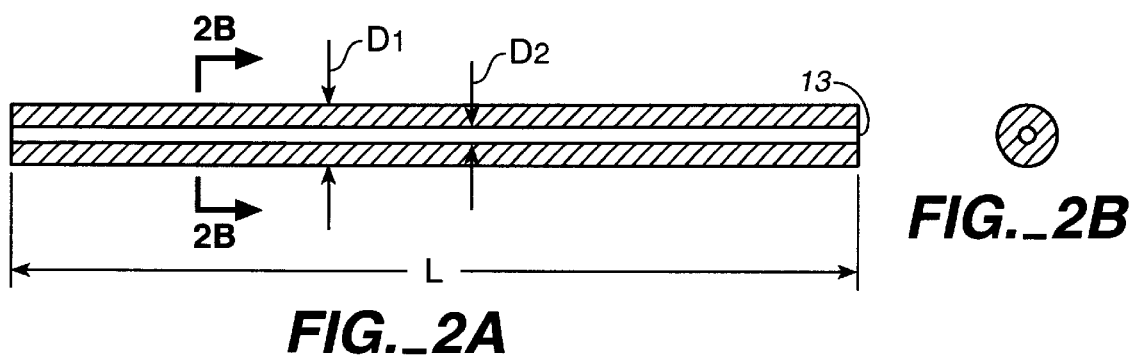
FIG._2A  FIG._2B

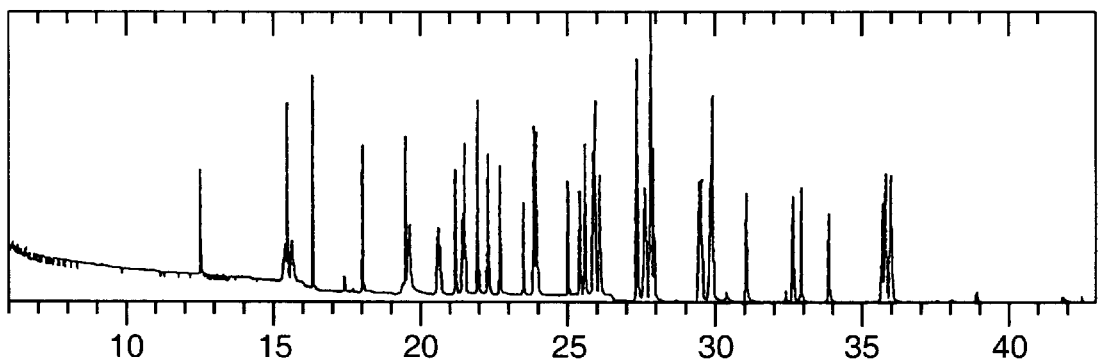
FIG._3A
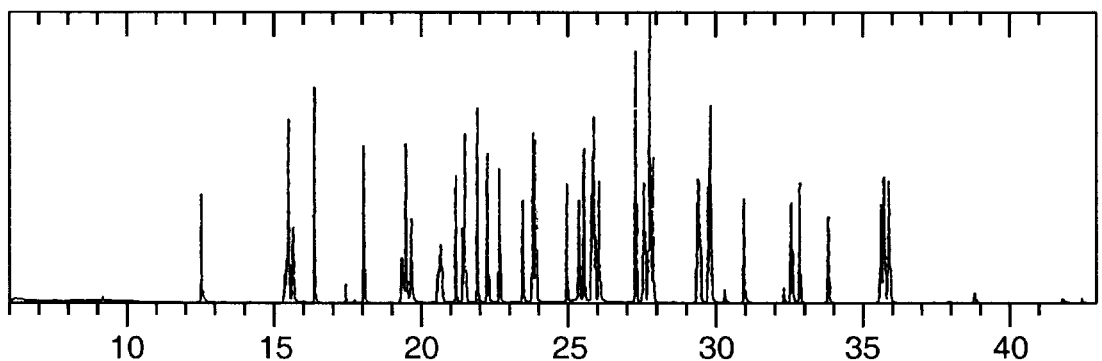
FIG._3B
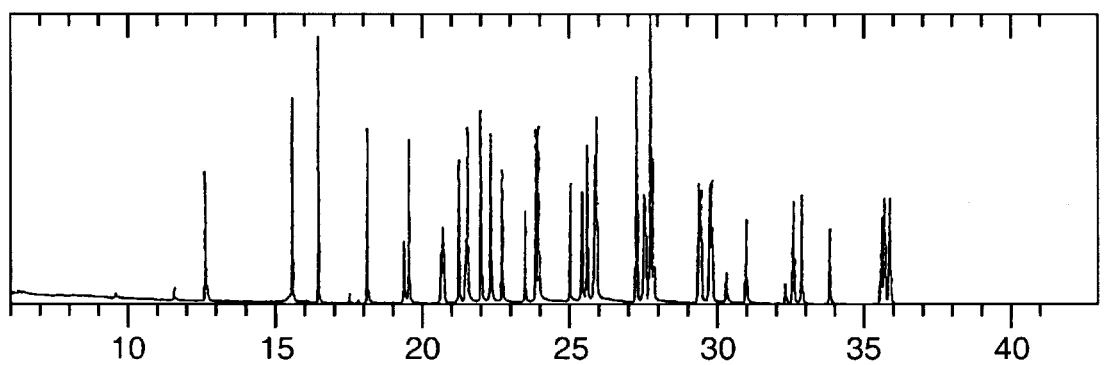
FIG._3C

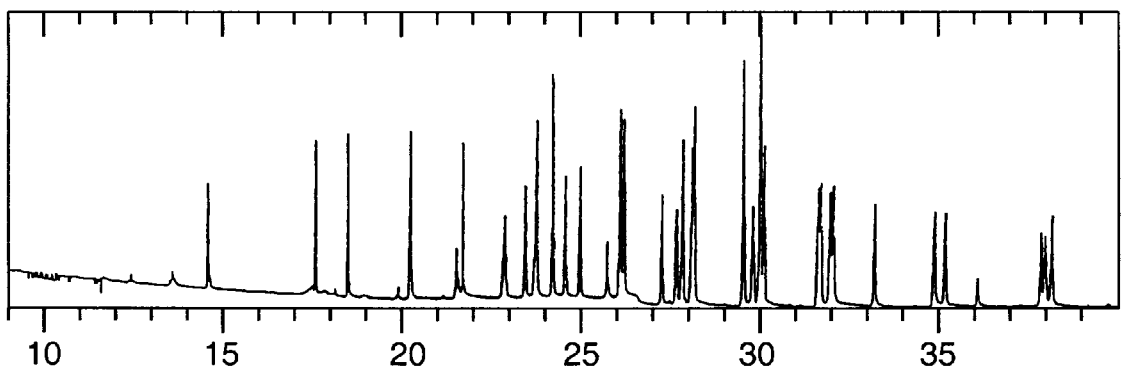
FIG._4A
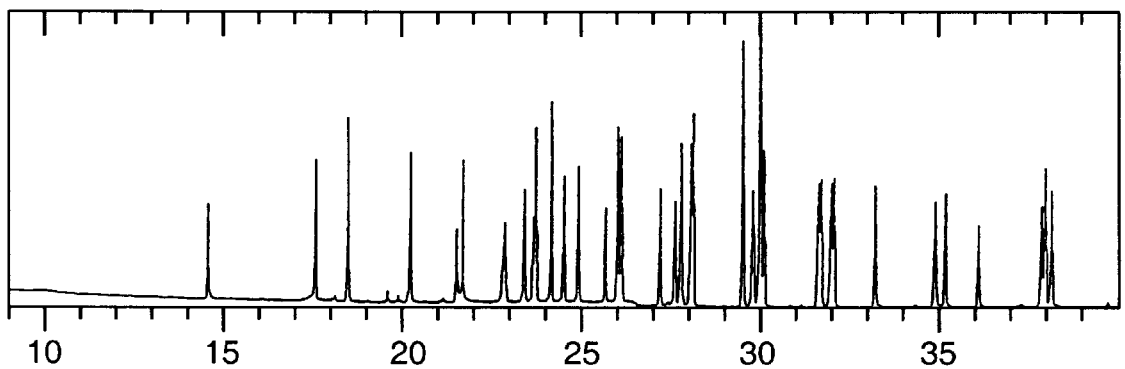
FIG._4B
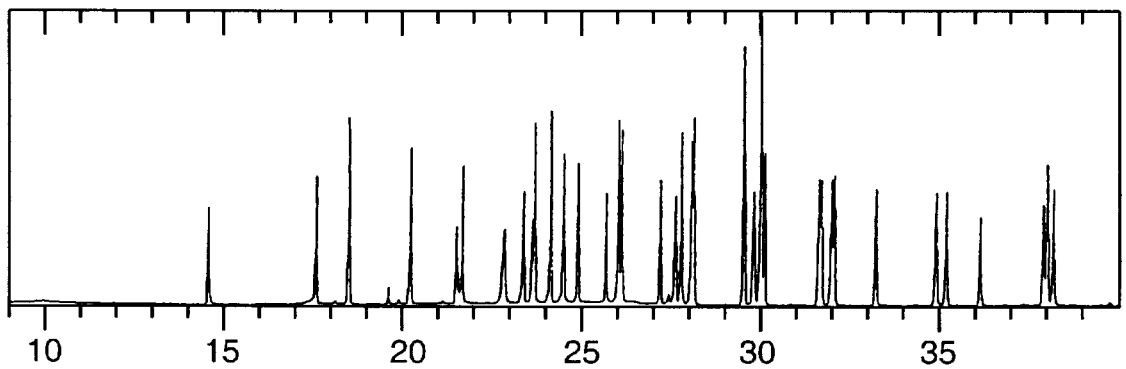
FIG._4C

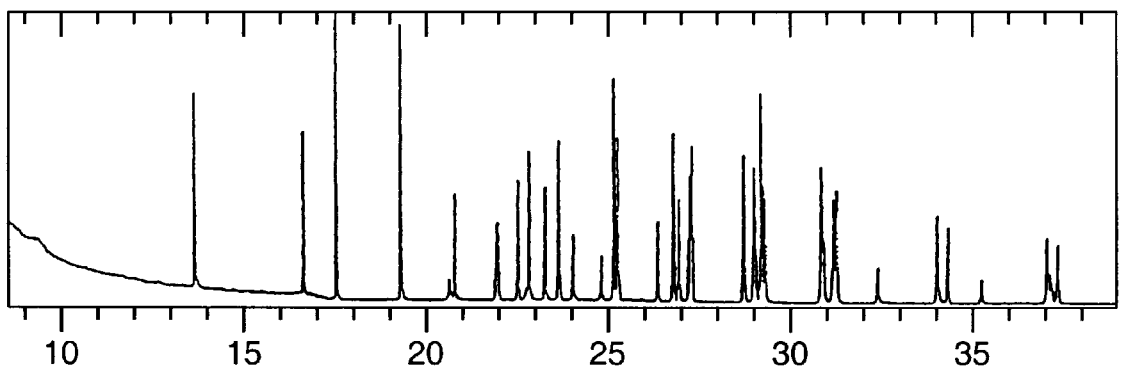
FIG._5A
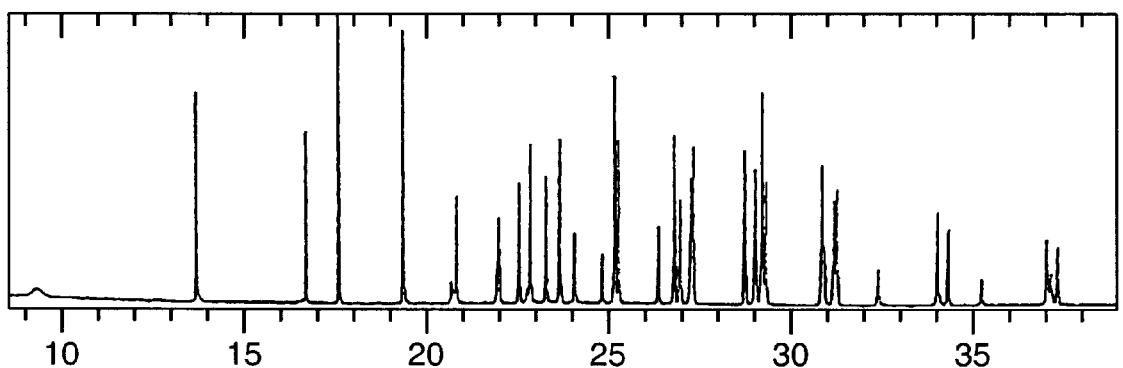
FIG._5B
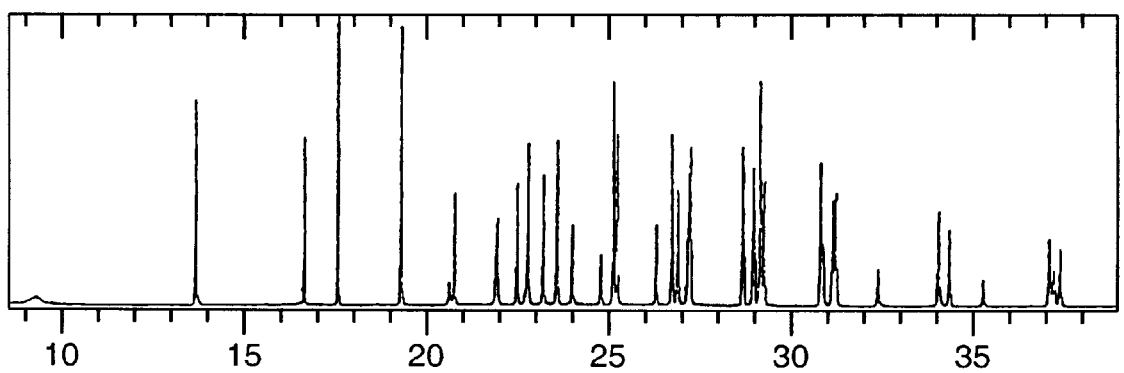
FIG._5C

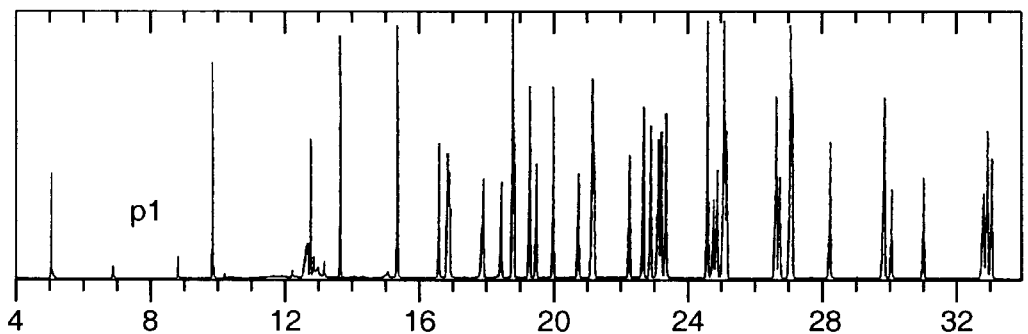
FIG._6A *(PRIOR ART)*
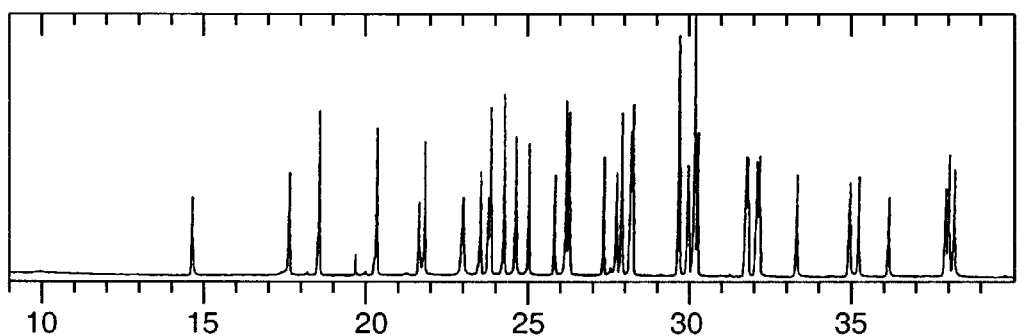
FIG._6B *(PRIOR ART)*
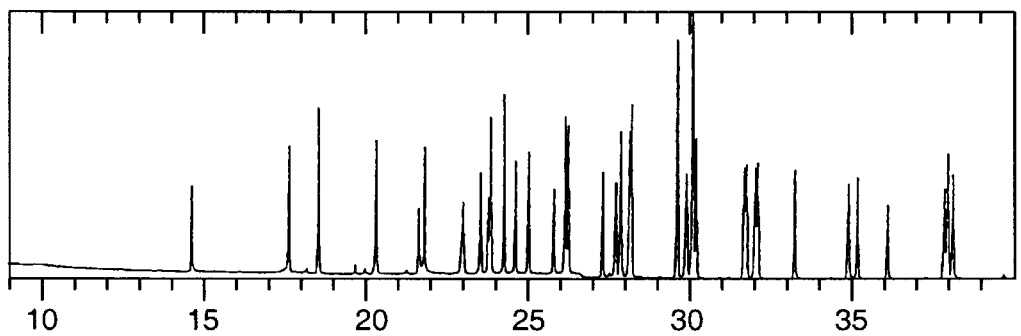
FIG._6C *(PRIOR ART)*
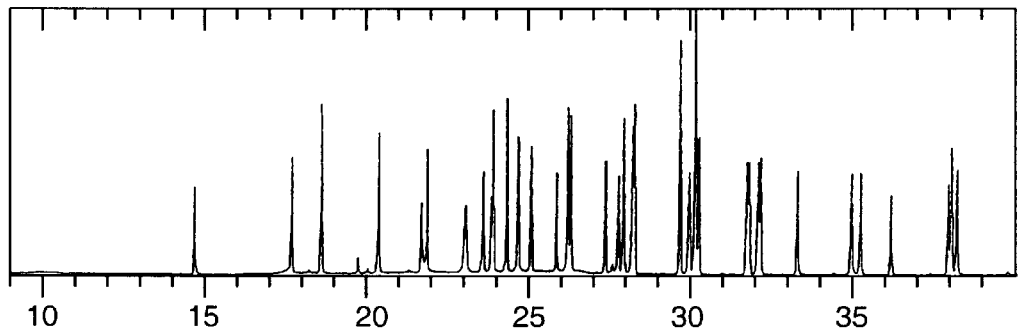
FIG._6D

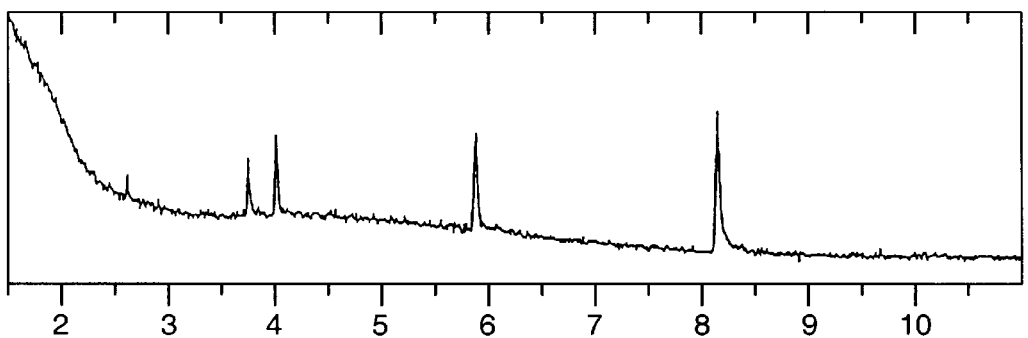
FIG._7A *(PRIOR ART)*
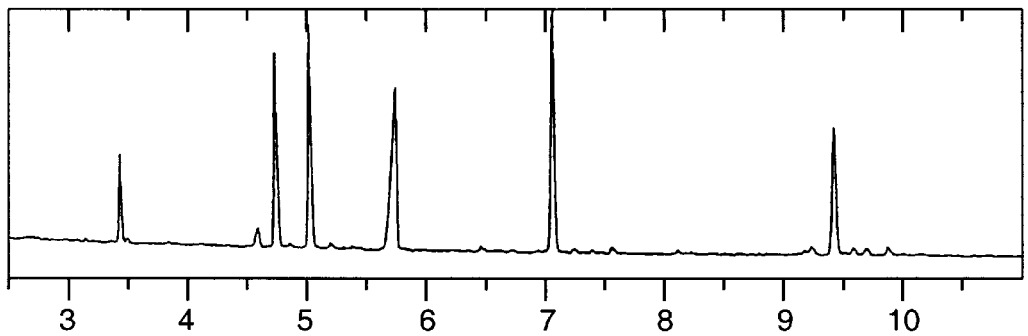
FIG._7B *(PRIOR ART)*
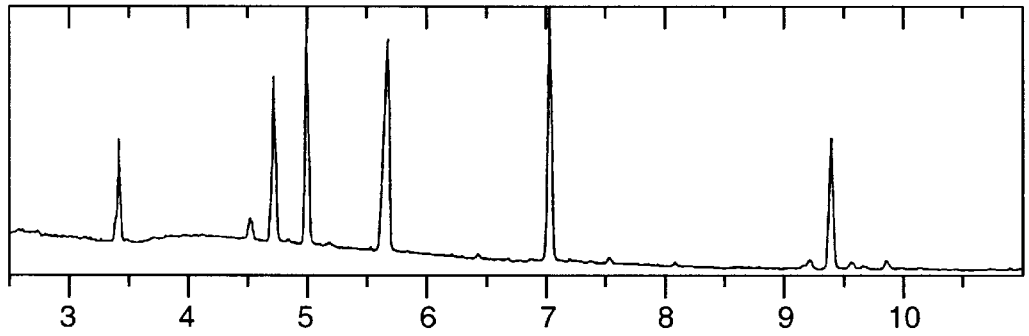
FIG._7C *(PRIOR ART)*
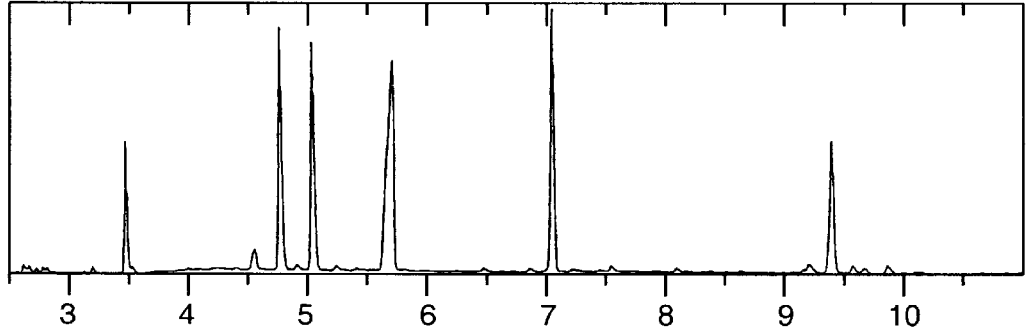
FIG._7D

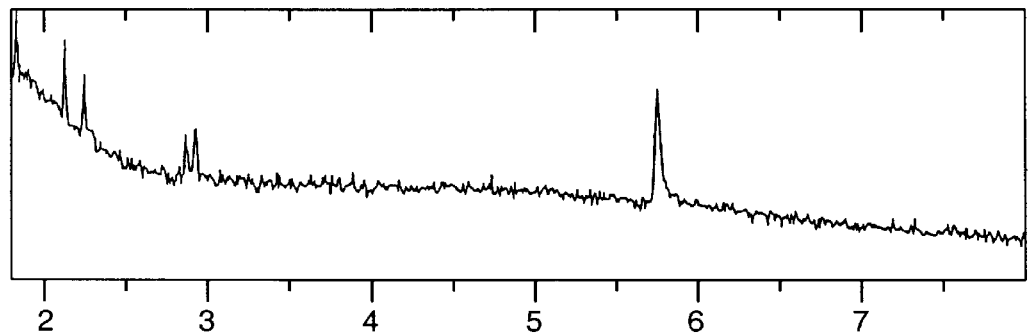
FIG._8A *(PRIOR ART)*
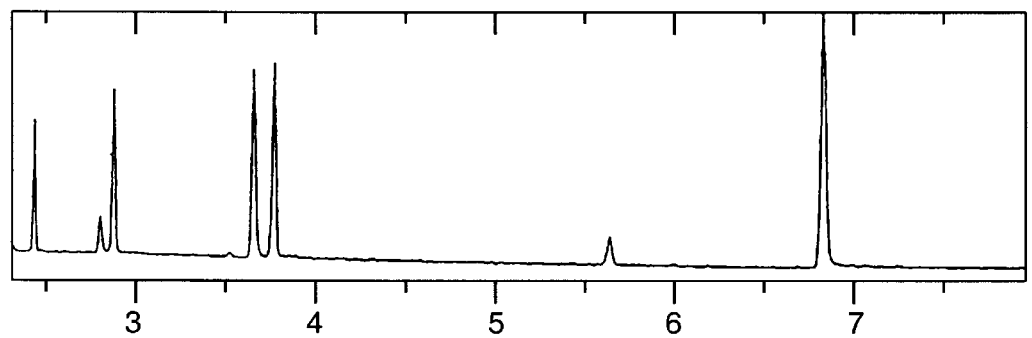
FIG._8B *(PRIOR ART)*
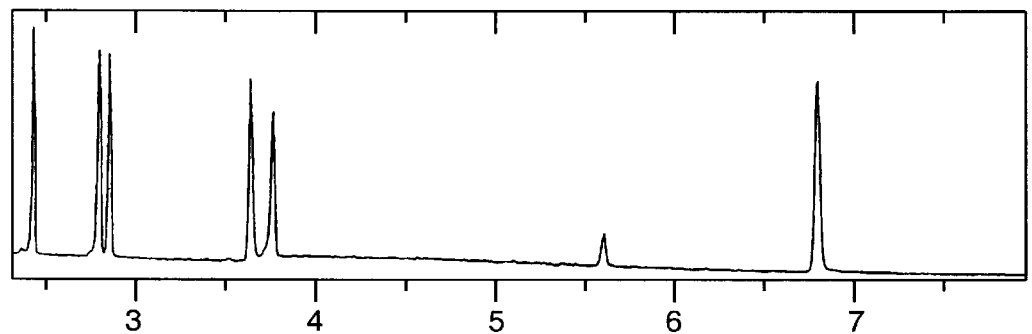
FIG._8C *(PRIOR ART)*
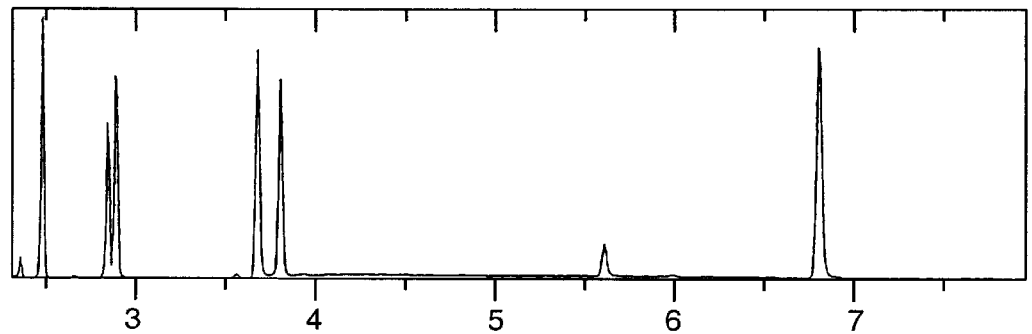
FIG._8D

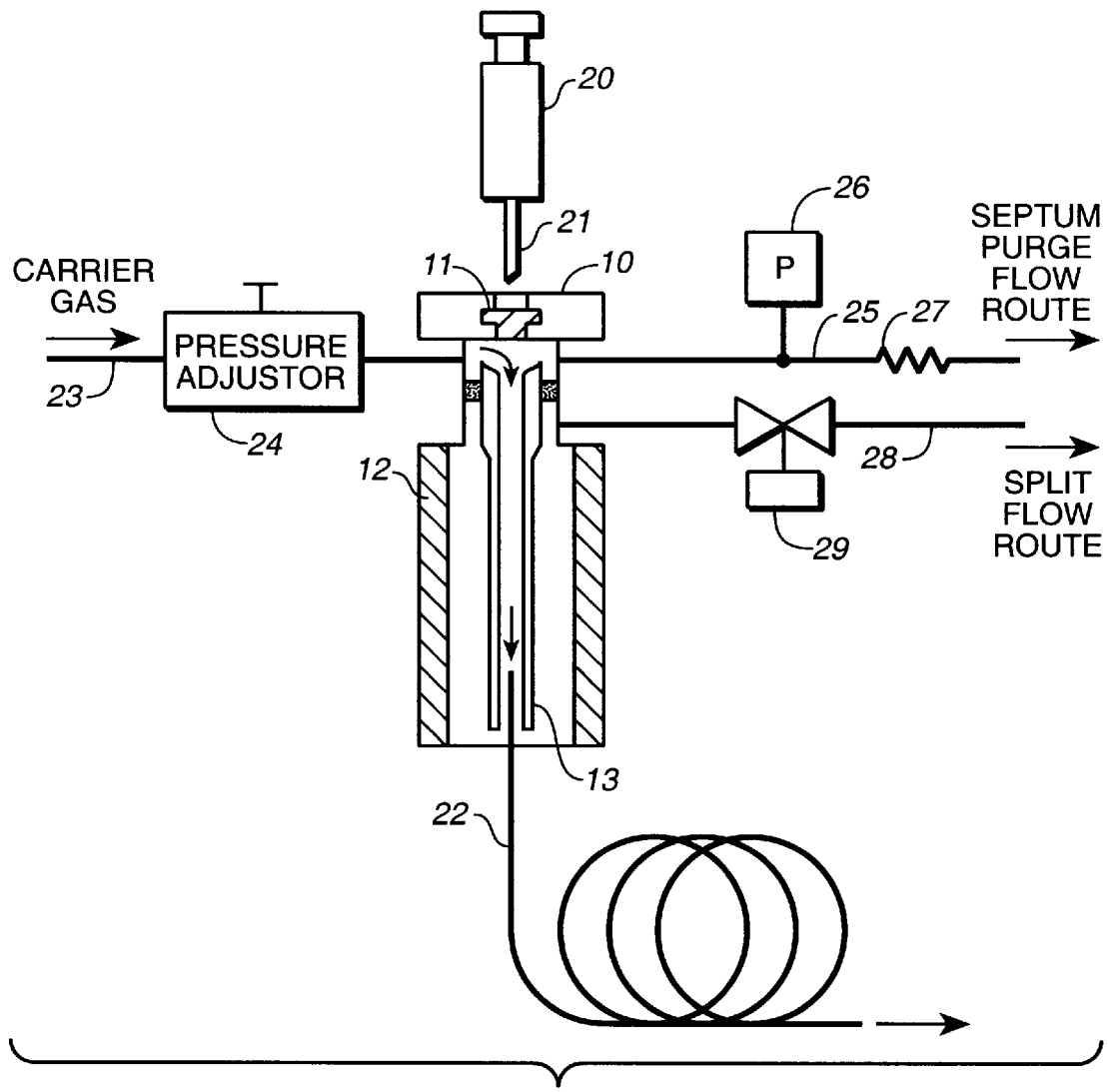
FIG._9A
(PRIOR ART)
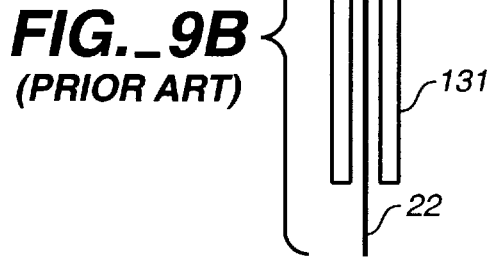
FIG._9B
(PRIOR ART)
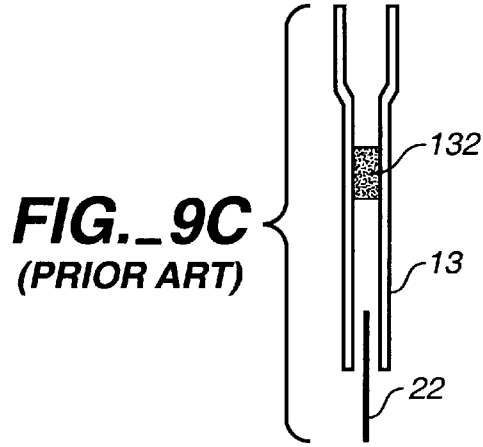
FIG._9C
(PRIOR ART)

METHOD AND APPARATUS IN GAS CHROMATOGRAPHY FOR INTRODUCING A SAMPLE

BACKGROUND OF THE INVENTION

This invention relates to a method of and apparatus for introducing a sample containing target components to be analyzed into a capillary column of a gas chromatograph through a vaporization chamber provided at the inlet of the column. Throughout herein words like "inject" and "injection" will be reserved for denoting the operation of causing a sample liquid from outside to be placed inside the vaporization chamber, and words like "introduce" and "introduction" will be used regarding the operation for transporting the sample inside the vaporization chamber into the column on a carrier gas flow.

As shown in FIG. 9A, a gas chromatograph usually has a vaporization chamber 10 at the inlet of a capillary column 22 and a septum 11 made, for example, of silicone rubber is placed at the top end of the vaporization chamber 10. A carrier gas flow route 23 for introducing a carrier gas (such as He) and a septum purge flow route 25 for removing gases generated from the septum 11 are connected to an upper part of the vaporization chamber 10. The carrier gas flow route 23 contains a pressure adjustor 24 by means of which the flow rate of the carrier gas being supplied into the vaporization chamber 10 can be controlled. The septum purge flow route 25 contains a pressure sensor 26 for detecting the pressure inside the vaporization chamber 10, as well as a flow resistor 27.

The vaporization chamber 10 is surrounded by a heater 12 and contains therein a tubular member (herein referred to as "the insert" 13) made, for example, of glass. A split flow route 28 containing an electromagnetic valve 29 is also connected to the vaporization chamber 10 for discharging the gas from the interior of the vaporization chamber 10. Prior to the injection of a sample, the pressure adjustor 24 is appropriately operated such that a carrier gas flows at a specified rate through the insert 13 inside the vaporization chamber 10 into the column 22. A needle 21 at the tip of a syringe 20 is then caused to penetrate the septum 11 and a sample liquid, normally consisting of target components to be analyzed and a solvent such as acetone and hexane, is injected.

For introducing the sample liquid injected into the vaporization chamber 10 further into the column 22 in a gas chromatograph as described above, there have been known several different methods such as the splitless method, the cold on-column method, and the programmed temperature vaporizer (PTV) method. In the splitless method, the heater 12 is controlled at a constant temperature such that the temperature inside the vaporization chamber 10 is maintained above the boiling points of the components to be analyzed and about 1–2 $\mu$l of a sample liquid is injected from the syringe 20 into the vaporization chamber 10 while the electromagnetic valve 29 in the split flow route 28 is kept closed. Since the interior of the vaporization chamber 10 is at a high temperature, the injected sample liquid is vaporized, is carried by the flow of the carrier gas, passes through the insert 13 and is introduced into the column 22. As the vaporized solvent remaining in the vaporization chamber 10 flows into the column 22 slowly over an extended length of time, the tailing of the solvent peak appears prominently on the chromatogram. After a specified length of time has elapsed since the injection of the sample, the valve 29 is opened and the vaporized solvent inside the vaporization chamber 10 is discharged to the exterior through the split flow route 28.

In the splitless analysis, components with relatively low boiling points vaporize instantly but components with high boiling points may not vaporize as easily. For this reason, it has been known to insert a filler such as glass wool into the insert 13 such that even components with high boiling points can vaporize more quickly, heated by the filler, and are introduced into the column 22. Thus, all components to be analyzed can be dependably vaporized and the repeatability of the analysis improves.

Even if non-volatile components are present, such components are withheld inside the insert 13 (or by the filler) and are prevented from entering the column 22. Contamination of the column 22 can thus be avoided, and the advantage is that the user has only the insert 13 (or the filler) to exchange.

Since the interior of the vaporization chamber 10 is always maintained at a high temperature in the splitless analysis; however, components which can be decomposed easily by heat may undergo thermal decomposition before they are introduced into the column 22. If the insert 13 is filled with a filler, furthermore, there is the possibility that the target components to be analyzed may be adsorbed or caused to decompose thereby.

In the cold on-column method, an adaptor 131 as shown in FIG. 9B, made for example of stainless steel, is used instead of the insert 13 of FIG. 9A and is set inside the vaporization chamber 10, the internal temperature of which is made controllable according to a program. The column 22 is inserted into this adaptor 131 such that its top end is directly below the septum 11. While the heater 12 is controlled so as to maintain the interior of the vaporization chamber 10 at a temperature below the boiling point of the solvent for the sample liquid, about 1–2 $\mu$l of the sample liquid is injected from the tip of the needle 21 directly into the column 22. The sample liquid thus injected is evaporated while passing through the column 22. By this method, therefore, the injected sample can be entirely introduced into the column 22 dependably without regard to the boiling points of its components. Since the vaporization chamber 10 is maintained at a low temperature, even those components which would decompose easily by heat can be introduced into the column 22 without undergoing thermal decomposition. If the sample liquid contains a non-volatile component, however, such a component pollutes the column 22 and a contaminated portion of the column 22 must be cut off. Since the sample liquid must be injected directly into the column 22 according to this method, furthermore, a special syringe 20 with needle 21 with a sufficiently small outer diameter must be used, and there is the danger of damaging the column 22.

In the PTV method, an insert 13 filled with a filler 132 as shown in FIG. 9C is usually used. The heater 12 is controlled such that the temperature inside the vaporization chamber 10 will be near the boiling point of the solvent when the sample is injected and will increase thereafter in a specified manner. At the time of the sample injection, the injected sample liquid is not completely vaporized because the temperature is relatively low and is temporarily held by the filler 132. As the temperature is raised, components are vaporized sequentially in the order of their boiling points and are transported by the flow of the carrier gas through the insert 13 into the column 22.

By this method, as by the splitless method, the valve 29 in the split flow route 28 must be opened after a certain length of time has elapsed such that the effect of the tailing of the solvent peak may be reduced. If this time is too long, the tailing of the solvent becomes too large. If this time is too short, the tailing can be made smaller, but some target components to be analyzed may be discharged to the exterior.

Each of the prior art methods described above has both advantages and disadvantages. Thus, when many components are analyzed at once by a single injection, some of the target components to be analyzed, such as those which decompose easily by heat and those with boiling points near that of the solvent, may not be appropriately introduced into the column 22 and may fail to be correctly analyzed.

SUMMARY OF THE INVENTION

It is therefore an object of this invention to provide a method of and an apparatus for dependably introducing various components with both high and low boiling points into a column in gas chromatography.

It is another object to provide such a method and an apparatus for reducing the variations in the base line of a chromatograni due to effects of the solvent.

It is still another object to provide such a method and an apparatus capable of introducing a sample into the column without causing it to undergo thermal decomposition.

A method and apparatus embodying this invention, with which the above and other objects can be accomplished, may be characterized by the use of a tubular insert with an inner volume significantly smaller than that of a prior art insert such that the retention time of the carrier gas will be less than 4 seconds and wherein the internal temperature of the vaporization chamber is kept within a specified range above the boiling point of the solvent of the sample liquid at the time of the sample injection so as to be lower than the boiling points of the target components to be analyzed and is thereafter increased in a specified manner.

In an apparatus for introducing a sample according to this invention, the flow rate of the carrier gas passing through the insert set inside the vaporization chamber is set within a standardized range of 1–3 ml/minute. If the carrier gas flow rate is 1 ml/minute, the inner volume of the insert must be less than about 0.07 ml in order that the retention time of the carrier gas be less than 4 seconds. Since standard inserts with inner volume about 0.2 ml are commonly being used, this means that an insert to be used according to this invention should have a significantly smaller inner volume (about ⅓) than conventionally used inserts. The reason for this choice is that the sample liquid injected into the vaporization chamber is introduced into the column mostly in a mist condition, that is, without being vaporized.

According to this invention, such an insert with a small internal volume is used without a filler to introduce the entire amount of injected sample into the column. At the time of the sample injection, the temperature inside the vaporization chamber is set not too high (say, by about 20–30° C.) above the boiling point of the solvent of the sample liquid to be injected. Thereafter, the temperature is controlled so as to rise according to a specified temperature curve.

Although the sample liquid is injected into the vaporization chamber as minute liquid droplets in the form of a mist, only a portion of the solvent in these droplets is vaporized immediately after the injection because the temperature is relatively low. While this mist-like sample liquid travels on the stream of gas towards the inlet of the column, the solvent in these droplets continues to vaporize and components with relatively low boiling points are also vaporized. Since the internal volume of the insert is small and the speed of the carrier gas therein is fast, the sample is introduced into the column within a relatively short period of time as a mixture of vaporized parts and minute liquid droplets.

Although a portion of the injected sample liquid may adhere to the inner wall of the insert, it is vaporized as the temperature of the vaporization chamber is raised and is introduced into the column by the stream of the carrier gas.

Since the injected sample liquid is not evaporated completely inside the vaporization chamber, its expansion in volume is accordingly smaller and it does not flow over from the insert to be caught inside the dead volume within the vaporization chamber. As a result, almost the entire amount of the sample liquid injected into the vaporization chamber can be quickly introduced into the column without sustaining a loss. Since the internal temperature of the vaporization chamber is maintained at a relatively low level for a while after the injection of the sample, even components susceptible to thermal decomposition can be introduced into the column without undergoing decomposition. Since most of the non-volatile components contained in the sample liquid is kept inside the insert, contamination of the column can be avoided.

According to a preferred embodiment of the invention, the flow rate of the carrier gas into the vaporization chamber is temporarily increased at the time of the sample injection. If the chromatograph is so structured that the gas flow rate is controllable by adjusting the carrier gas pressure, this may be accomplished by increasing this pressure momentarily at the time of sample injection and returning it to the original level after a specified length of time has elapsed thereafter. If the flow rate of the carrier gas is thus increased, the time required for introducing the sample into the column can be shortened, that is, the efficiency of sample introduction can be improved.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a block diagram of an apparatus embodying this invention for introducing a sample into a gas chromatograph;

FIG. 2A is an longitudinal sectional view of the insert shown in FIG. 1 and FIG. 2B is a sectional view of the same insert taken along line 2B—2B of FIG. 2A;

FIGS. 3A, 3B, and 3C are chromatograms for showing the effects of initial temperature;

FIGS. 4A, 4B, and 4C are chromatograms for showing the effects of the internal volume of the insert;

FIGS. 5A, 5B, and 5C are chromatograins for showing the effects of the gas pressure at the time of sample injection;

FIGS. 6A–6D, 7A–7D, and 8A–8D are chromatograms for showing the effects of the method according to this invention, as compared to prior art methods; and FIG. 9A is a block diagram of a prior art apparatus for introducing a sample into a gas chromatograph, FIG. 9B is a sectional view of a prior art insert and a portion of a column therefor, and FIG. 9C is a sectional view of another prior art insert with a portion of a column therefor.

Throughout herein, like components are indicated by the same numerals even where they indicate like components of different apparatus and they may not necessarily be described repetitiously.

DETAILED DESCRIPTION OF THE INVENTION

The invention is described next by way of an example with reference to FIGS. 1–5. FIG. 1 is a block diagram of a sample introducing apparatus for a gas chromatograph according to this invention which is similar to the prior art apparatus described above with reference to FIG. 9A, but its significant difference therefrom is that its vaporization chamber 10 contains therein an insert 13 with a significantly smaller internal volume. Explained more in detail, while an insert with standard internal diameter of about 1.6 mm is used for a capillary column with internal diameter of about 0.25–0.32 mm when a conventional PTV method is used, a much narrower tube with smaller internal volume is used as the insert 13 according to this invention. FIGS. 2A and 2B show such a capillary tube with length L=95 mm, outer diameter D1=40 mm and inner diameter D2=0.8 mm, its inner volume being 0.05 ml. At a standard carrier gas flow rate of 1–3 ml/minute, the retention time for a gas therein at the time of sample injection becomes about 1–3 seconds.

In FIG. 1, numeral 31 indicates a temperature controller for controlling the heater 12 such that the internal temperature of the vaporization chamber 10 is maintained at the time of sample injection at a specified level which is higher than the boiling point of the sample liquid but is not too high thereabove, that it is kept at this level for a specified length of time after the sample injection and that it is increased thereafter according to a specified program (or a temperature curve). Since the initial temperature for this temperature program must be changed according to the kind of the solvent being used, the temperature controller 31 may be so structured as to allow the user to input therethrough or to allow the user to merely select the kind of the solvent, automatically setting an appropriate initial temperature according to the selected kind of the solvent.

In FIG. 1, numeral 30 indicates a pressure controller which is basically for controlling the pressure adjustor 24 such that the value of the gas pressure inside the vaporization chamber 10 as monitored by the pressure sensor 26 will become, and remain at, a specified target level. In this manner, the carrier gas can be controlled to flow through the column 22 at a specified flow rate. The pressure controller 30 also serves to increase the gas pressure temporarily at the time of the sample injection (say, for 10 minutes from the starting time of the sample injection).

The sample injection is carried out as before by causing a needle 21 at the tip of a syringe 20 to penetrate a septum 11 and injecting the sample liquid into the vaporization chamber 10. The injected sample liquid will spread like a mist. Since the temperature inside the vaporization chamber 10 at this time is close to the boiling point of the solvent, a portion of the solvent, which nevertheless amounts to a major portion of the minute liquid droplets, is evaporated. A major portion of the target components to be analyzed, contained in the sample liquid, remains in the liquid droplets without evaporating because their boiling points are higher than the temperature inside the vaporization chamber 10 at this time. The carrier gas, which has entered the vaporization chamber 10 through the carrier gas flow route 23, now advances downward inside the insert 13 from its upper opening. The mist-like sample liquid containing evaporated solvent is carried by this gas flow to pass inside the insert 13 and reaches the inlet of the column 22. Since the internal volume of the insert 13 is small, the sample liquid reaches the inlet of the column 22 very quickly but the solvent in these liquid droplets continues to vaporize in the meantime.

As a result, the injected sample is introduced into the column 22 as a mixture of a gas (the already vaporized sample liquid) and a liquid (minute droplets). Because components with high boiling points in the droplets are not vaporized immediately, a part thereof adheres as a liquid to the inner wall of the insert 13 and remains there even after a major part of the mist-like sample has entered the column 22. Since the temperature inside the vaporization chamber 10 is raised thereafter, these components with high boiling points remaining on the inner wall of the insert 13 are vaporized sequentially as the internal temperature of the vaporization chamber reaches their boiling points and are introduced by the gas flow into the column 22. In summary, by a method according to this invention, the entire amount of the injected sample can be introduced into the column 22 while the valve 29 in the split flow route 28 is kept closed.

The effects of various parameters in the method of sample introduction according to this invention on the results of analysis will be explained next.

(i) Initial Temperature at the Time of Sample Injection

FIGS. 3A, 3B, and 3C are an example of total ion chromatograms representing the measured results when the initial temperature of the vaporization chamber 10 at the time of the sample injection was respectively 50° C., 90° C. and 140° C. The sample was a kind of water-based agricultural herbicide for golf courses diluted to 5 mg/l with acetone (boiling point=56° C.) as solvent, and 2 $\mu$l of this sample was injected. A mass spectrograph was used as the detector for the gas chromatograph but detectors of other kinds could be used. The temperature inside the vaporization chamber was kept at the initial temperature for 5 minutes after the sample injection and was raised thereafter uniformly at the rate of 10° C./minute until it became 260° C. The gas pressure at the time of the sample injection was 100 kPa with the gas flow rate equal to 4.9 ml/minute. After this gas pressure was maintained for 2 minutes, it was returned to 30 kPa (with gas flow rate of 2.1 ml/minute). Since the gas pressure does not drop all at once, it actually takes several tens of seconds to several minutes for the gas pressure to drop to the specified level. The internal diameter and the length of the column were 0.32 mm and 30 m, and He was used as the carrier gas.

If the temperature of the insert 13 is lower than the boiling point of the solvent as shown in FIG. 3A, the tailing of the solvent lasts for a relatively long period of time (about 27 minutes) after the specified amount of the sample is injected. This is probably because the initial temperature is too low and the acetone which occupies a large portion of the sample liquid injected into the vaporization chamber 10 remains without evaporating and stays at a lower part of the insert 13, gradually evaporating and entering the column 22. Thus, the effect of the solvent lasts for a long time.

If the temperature of the insert 13 is far higher than the boiling point of the solvent, as shown in FIG. 3C, the tailing of the solvent lasts also for a relatively long period of time (about 21 minutes), although not as long as in the case of FIG. 3A. This may be because the initial temperature is so high that acetone in the sample liquid injected into the vaporization chamber 10 is evaporated and expands rapidly and the evaporated solvent flows over from the insert 13, becoming captured in the dead volumes inside the vaporization chamber 10 and gradually entering the column 22 thereafter.

If the initial temperature is set at an appropriate level which is higher than the boiling point of the solvent, as shown in FIG. 3B, the tailing of the solvent is hardly observed. This may be because, if the initial temperature is appropriately set, the minute droplets of the sample liquid injected through the tip of the needle 21 reach the inlet of the column 22 slowly and the solvent inside these droplets, as well as components with low boiling points, evaporates at an appropriate speed in the meantime such that it is a mixture of minute liquid droplets and partially vaporized solvent that is introduced into the column 22.

(ii) Internal Volume of the Insert

FIGS. 4A, 4B, and 4C are an example of gas chromatograms when the internal diameter of the insert 13 was respectively 2.0 mm, 1.2 mm, and 0.8 mm. The length of the insert 13 was 95 mm in all cases. Thus, the internal volume of the inserts was respectively 0.3 ml, 0.2 ml and 0.05 ml. When the carrier flow rate at the time of sample injection was at a standard value of 1–3 ml/minute, the retention time of the carrier gas inside the insert 13 was respectively 6–18 seconds, 4.2–12 seconds, and 1.02–3 seconds. The initial temperature inside the vaporization chamber was set at 90° C. and the pressure of the carrier gas was set at the initial value of 100 kPa for about 2 minutes and then changed to 30 kPa.

FIG. 4A, 4B, and 4C show that the tailing of the solvent is greater if an insert with a larger internal volume is used. This is probably because the solvent which has evaporated inside the insert is dispersed if the internal volume of the insert is large. The retention time values given above are values obtained under the assumption that the carrier gas introduced into the insert is smoothly introduced into the column. In reality, however, the flow of the carrier gas does not take place smoothly if the internal volume is too large and a portion of the gas remains for an extended period of time beyond the presumed retention time. As a result, the evaporated solvent mixed with such a carrier gas is introduced into the column only gradually, giving results for an extended length of time. Thus, it may be understood that a significant result can be obtained if use is made of an insert with an internal volume which will cause a retention time of less than about 4 seconds.

(iii) Pressure of Carrier Gas

FIGS. 5A, 5B, and 5C are an example of gas chromatograms when the pressure of the carrier gas was respectively at the initial pressure of 30 kPa, at the initial pressure of 60 kPa for about 10 minutes and then changed to 30 kPa, and at the initial pressure of 100 kPa for about 2 minutes and then changed to 30 kPa with the internal diameter and the length of the insert respectively 0.8 mm and 95 mm, the initial temperature being 90° C. in all cases.

Since a portion of the sample liquid injected into the vaporization chamber is vaporized immediately thereafter, its volume increases rapidly. Thus, the amount of injection cannot be made large in the case of an insert with an internal volume as described above in fear of the injected mist-like sample overflowing from the insert, and this is a disadvantage from the point of view of sensitivity of analysis due to the smallness of the amounts of target components to be analyzed. If the flow rate of the carrier gas is temporarily increased at the time of sample injection so as to temporarily increase the gas pressure inside the insert, the injected sample can be transported towards the inlet of the column without overflowing from the insert.

If the gas pressure is not increased at the time of the sample injection, as shown in FIG. 5A, the effect of the solvent tailing is prominent, This is probably because the vaporized solvent flowing over the insert was captured in the dead volumes of the vaporization chamber and entered slowly into the column over an extended period of time. If the pressure is temporarily raised as shown in FIGS. 5B and 5C, the overflow of the vaporized solvent is prevented by the pressure of the carrier gas and the tailing of the solvent can be avoided.

Next, the invention is explained, as applied to the water quality analysis according to the Water Law (of Japan). FIGS. 6A, 6B, 6C, and 6D are results of analysis on agricultural herbicide for golf courses (such as isoxythion), FIGS. 7A, 7B, 7C, and 7D are those of methyl haloacetate derivatives (HAME), and FIGS. 8A, 8B, 8C, and 8D are those of a disinfection by-product (such as formaldehyde). FIGS. 6A, 7A, and 8A are results obtained by the prior art splitless method, FIGS. 6B, 7B, and 8B are by the prior art cold on-column method, FIGS. 6C, 7C, and 8C are by the prior art PTV method, and FIGS. 6D, 7D, and 8D are by the gas chromatographic analysis using the method of introduction embodying this invention.

Agricultural herbicides for golf courses contain components which easily decompose by heat. Thus, FIG. 6A shows the appearance of a peak p1 of a product due to such thermal decomposition if the prior art splitless method is used. In other words, FIG. 6A shows that the splitless method is suitable for the analysis of such a target sample. By the cold on-column method and the PTV method, on the other hand, the tailing of the solvent is prominent. In the case of the cold on-column method, this is because, as the sample liquid is directly injected from a needle into the column of an extremely small diameter, a portion of the sample liquid flows over the column and the effect of the solvent within the sample liquid remains over a long period of time. In the case of the PTV method, this is due to the effect of the portion of the sample liquid which remains at the bottom of the vaporization chamber, as explained above. By the method according to this invention, by contrast, FIG. 6D shows that there is no effect of thermal decomposition and that the tailing of the solvent is small, the baseline of the chromatogram being stable.

As for HAME and disinfection by-products, since they contain components with relatively low boiling points which are close to that of the solvent, there are several peaks of these components near the solvent's peak. By the prior art methods, the tailing of the solvent is prominent, as shown in FIGS. 7A–7C and 8A–8C. In the case of the splitless method in particular, the peaks which appear during the initial period are nearly buried by the tailing. By the method of the present invention, by contrast, the tailing of the solvent is nearly totally absent and hence even the peaks of components with boiling points near that of the solvent can be detected with high sensitivity, as shown in FIGS. 7D and 8D.

In summary, the method and apparatus according to this invention have many advantages. Firstly, samples in a wide range with components having high to low boiling points can be introduced into the column although it was difficult by prior art methods and apparatus. Moreover, even those components which decompose easily by heat can be introduced into the column without decomposing. Thus, the method of introducing the sample need not be changed according to the target components to be analyzed. The analysis can thus be carried out efficiently and a sample containing all these different kinds of target components can be analyzed at once. Secondly, since the sample can be introduced into the column efficiently, the tailing of the solvent becomes small and the baseline of the chromatogram stabilizes. As a result, the peaks of the solvent and components with low boiling points can be clearly separated. Thirdly, since no filler is used inside the insert, there is no danger of adsorption or decomposition of the sample components due to its presence. Fourthly, unlike the prior art cold on-column method by which the sample liquid is directly injected into the column and the column becomes quickly contaminated with non-volatile substances such that it becomes necessary to cut or replace the column frequently, the present invention eliminates contamination of the column because the non-volatile components remain inside the insert or where it connects with the column. As a result, many samples can be analyzed continuously and damage to the column can be avoided. Fifthly, unlike the prior art cold on-column method, the present invention does not require any special kind of micro-syringe for inserting the needle into the column. A micro-syringe of an ordinary kind can be used and hence the apparatus has better durability and the injection can be carried out with higher reliability. The cost of analysis is also reduced according to this invention.

What is claimed is:

1. A method of introducing into a capillary column of a gas chromatograph a sample, which contains target components to be analyzed and a solvent and is injected into a vaporization chamber at the inlet of said column, by causing a carrier gas to flow into said vaporization chamber and to carry said injected sample into said column, said method comprising the steps of:

temporarily increasing the pressure of said carrier gas flowing into said vaporization chamber as said sample is injected;

causing said carrier gas to introduce said sample through a tubular insert which is inserted into said vaporization chamber and has an internal volume so determined that the retention time of said carrier gas through said insert is less than 4 seconds; and controlling the temperature inside said vaporization chamber to remain within a specified range above the boiling point of said solvent as said sample is injected into said vaporization chamber and thereafter raising the temperature inside said vaporization chamber.

2. The method of claim 1 wherein temperature inside said vaporization chamber is increased to a final temperature above the boiling points of said target components.

3. The method of claim 2 wherein said specified range is such that the temperature inside said vaporization chamber is higher than the boiling points of said target components.

4. The method of claim 3 wherein said specified range is 20° C. to 30° C.

5. The method of claim 3 further comprising the step of temporarily increasing the pressure of said carrier gas flowing into said vaporization chamber as said sample is injected.

6. The method of claim 2 further comprising the step of temporarily increasing the pressure of said carrier gas flowing into said vaporization chamber as said sample is injected.

7. The method of claim 1 wherein said specified range is such that the temperature inside said vaporization chamber is higher than the boiling points of said solvent.

8. The method of claim 7 wherein said specified range is 20° C. to 30° C.

9. The method of claim 7 further comprising the step of temporarily increasing the pressure of said carrier gas flowing into said vaporization chamber as said sample is injected.

10. An apparatus for supplying a carrier gas into a vaporization chamber at an inlet of a capillary column of a gas chromatograph for introducing into said column a sample which contains target components to be analyzed and a solvent and is injected into said vaporization chamber, said apparatus comprising:

a tubular insert disposed inside said vaporization chamber for causing said carrier gas and said sample to pass therethrough into said column, said insert having an internal volume such that the retention time of said carrier gas through said insert is less than 4 seconds;

a pressure control means for controlling the pressure of said carrier gas entering said vaporization chamber, said pressure control means temporarily increasing the pressure of said carrier gas flowing into said vaporization chamber as said sample is injected; and a heater which is controlled to maintain the temperature inside said vaporization chamber within a specified range above the boiling point of said solvent as said sample is injected into said vaporization chamber and to thereafter raise the temperature inside said vaporization chamber.

11. The apparatus of claim 10 wherein said heater is controlled to raise the temperature inside said vaporization chamber to a final temperature above the boiling points of components in said sample to be analyzed.

12. The apparatus of claim 11 wherein said specified range is such that the temperature inside said vaporization chamber is higher than the boiling points of said target components.

13. The apparatus of claim 12 wherein said specified range is 20° C. to 30° C.

14. The apparatus of claim 12 further comprising a pressure control means for controlling the pressure of said carrier gas entering said vaporization chamber, said pressure control means temporarily increasing the pressure of said carrier gas flowing into said vaporization chamber as said sample is injected.

15. The apparatus of claim 11 further comprising a pressure control means for controlling the pressure of said carrier gas entering said vaporization chamber, said pressure control means temporarily increasing the pressure of said carrier gas flowing into said vaporization chamber as said sample is injected.

16. The apparatus of claim 10 wherein said specified range is such that the temperature inside said vaporization chamber is higher than the boiling points of said solvent.

17. The apparatus of claim 16 wherein said specified range is 20° C. to 30° C.

18. The apparatus of claim 16 further comprising a pressure control means for controlling the pressure of said carrier gas entering said vaporization chamber, said pressure control means temporarily increasing the pressure of said carrier gas flowing into said vaporization chamber as said sample is injected.

* * * * *